United States Patent
Gladue et al.

(10) Patent No.: US 6,812,009 B2
(45) Date of Patent: Nov. 2, 2004

(54) DHA-CONTAINING NUTRITIONAL COMPOSITIONS AND METHODS FOR THEIR PRODUCTION

(75) Inventors: Raymond M. Gladue, Lexington, KY (US); Paul W. Behrens, Ellicott City, MD (US)

(73) Assignee: Martek Biosciences Corporation, Columbia, MD (US)

( * ) Notice: Subject to any disclaimer, the term of this patent is extended or adjusted under 35 U.S.C. 154(b) by 54 days.

(21) Appl. No.: 10/082,340

(22) Filed: Feb. 26, 2002

(65) Prior Publication Data

US 2002/0123111 A1 Sep. 5, 2002

Related U.S. Application Data

(62) Division of application No. 09/529,021, filed on Apr. 6, 2000, which is a continuation of application No. PCT/US98/15835, filed on Jul. 31, 1998.
(60) Provisional application No. 60/054,563, filed on Aug. 1, 1997.

(51) Int. Cl.⁷ .............................. C12P 7/64; C12N 1/12; C12N 1/14; A23D 9/00
(52) U.S. Cl. ................. 435/134; 435/254.1; 435/257.3; 426/601; 426/602
(58) Field of Search ................................ 426/601, 602; 435/134, 137, 254.1, 257.3

(56) References Cited

U.S. PATENT DOCUMENTS

| | | |
|---|---|---|
| 5,000,888 A | 3/1991 | Kilbride, Jr. et al. |
| 5,104,668 A | 4/1992 | Cole et al. |
| 5,130,242 A | 7/1992 | Barclay |
| 5,397,591 A | 3/1995 | Kyle et al. |
| 5,407,957 A | 4/1995 | Kyle et al. |
| 5,492,938 A | 2/1996 | Kyle et al. |
| 5,550,156 A * | 8/1996 | Kyle .......................... 514/547 |
| 5,688,500 A | 11/1997 | Barclay |
| 5,711,983 A | 1/1998 | Kyle et al. |

FOREIGN PATENT DOCUMENTS

| | | |
|---|---|---|
| WO | WO 9803671 | 1/1998 |
| WO | WO9937166 | 7/1999 |
| WO | WO9965327 | 12/1999 |

* cited by examiner

Primary Examiner—Jon P. Weber
Assistant Examiner—Kailash C. Srivastava
(74) Attorney, Agent, or Firm—Hunton & Williams LLP

(57) ABSTRACT

This invention provides a particulate material suitable for use as a nutritional supplement, particularly as an aquaculture feed. The particulate material has a high proportion of DHA residues in the lipid fraction, which may be up to 35% of the material, or even more. Preferably, the material has a mean particle size of from about 5 microns to about 10 microns. This invention also provides a method for preparing a particulate material suitable for use as an aquaculture feed from microbial biomass, preferably from algal cells having a high content of DHA residues, by obtaining a lipid fraction from the biomass, preferably by solvent extraction of broken cells, followed by separating a fraction containing phospholipids and proteins from the lipid fraction, and removing water from the protein/phospholipid fraction to form a low moisture particulate, preferably by spray-drying the protein/phospholipid fraction.

36 Claims, No Drawings

DHA-CONTAINING NUTRITIONAL COMPOSITIONS AND METHODS FOR THEIR PRODUCTION

This application is a divisional of prior application Ser. No. 09/529,021 filed Apr. 6, 2000 which is a continuation of PCT/US98/15835, filed Jul. 31, 1998, complete application based on Provisional Application No. 60/054,563 filed Aug. 1, 1997.

BACKGROUND OF THE INVENTION

The last decade has witnessed a decline in the resources of natural fisheries that has now reached a level of global environmental crisis. Thirteen of the worlds seventeen major fisheries are classified by the United Nations Food and Agriculture Organization (F.A.O.) to be in peril or in steep decline. Even in the best case scenario of both maintaining the fishery catch at a record 100 million metric tons and conservative population growth, there will be a shortfall in global seafood supply by the end of this decade for the first time in human history. Furthermore, per capita global seafood consumption is predicted to increase as the worlds population shifts during the next two decades from industrialized countries to todays undeveloped and emerging economies; traditionally large consumers of seafood. The only way to meet the global demand for seafood by the year 2000 is if aquaculture replaces the insufficient natural fisheries catch.

Expansion of the aquaculture industry requires that several significant problems be addressed, and one of the most significant hurdles to establishing and maintaining an economically viable aquaculture operation is the difficulty of supplying nutritionally balanced feeds. Larval fish, bivalves and crustaceans raised in the wild consume a mixed population of feed organisms that collectively provide balanced nutrition. On the other hand, fish larvae, bivalves and crustaceans raised in aquaculture farms can be difficult to rear and require live feeds (algae or algae-fed rotifers and Artemia) for their nutrition. These live feeds are difficult to produce and maintain, require high labor inputs and specialized facilities, and as a result larval feeds constitute a significant cost to the aquaculture industry.

It is important that aquaculture feeds be nutritionally balanced so that the larvae receive proper nutrition. DHA (docosahexaenoic acid) has been identified as an important nutrient that contributes significantly to larval growth and survival (Fulks, W and K L Main (eds). 1991. "Rotifer and Microalgae Culture Systems. Proceedings of a US-Asia Workshop." Honolulu, Hi. The Oceanic Institute. Tamaru, CS, C S Lee and H Ako, 1991. "Improving the larval rearing of striped mullet (Mugil cephalus) by manipulating quantity and quality of the rotifer, *Brachionus plicatilis*." In: W. Fulks and K L Main (eds), 1991). Larvae ultimately acquire these fatty acids from algae, either by directly feeding on algae with high levels of polyunsaturated fatty acids or by feeding on rotifers and Artemia that have been reared on algae high in polyunsaturated fatty acids. Unfortunately, the algae, artemia and rotifers used at aquaculture farms are low in DHA, reducing the survival rates for the larvae below their maximal rate and increasing the cost of the final aquaculture farm product. If sufficient DHA could be provided to the larvae it is expected that the survival rate for larvae would increase, thus reducing the cost of farm-raised seafood.

SUMMARY OF THE INVENTION

In one embodiment, this invention provides a particulate material suitable for use as an aquaculture feed. The particulate material has a high proportion of DHA residues in the lipid fraction, which may be up to 35% of the material. Preferably, the material has a mean particle size of from about 5 microns to about 10 microns.

In another embodiment, this invention provides a method for preparing a particulate material suitable for use as an aquaculture feed from microbial biomass, preferably from algal cells having a high content of DHA residues, by obtaining a lipid fraction from the biomass, preferably by solvent extraction of broken cells, followed by separating a fraction containing phospholipids and proteins from the lipid fraction, and removing water from the protein/phospholipid fraction to form a low moisture particulate, preferably by spray-drying the protein/phospholipid fraction.

In still another embodiment, this invention provides a particulate material containing phospholipids having docosahexaenoic acid (DHA) residues, the particulate material being prepared by drying a slurry comprising a polar lipid extract from DHA-containing microbes, and dry, particulate material may be prepared from a slurry which is substantially free of material that did not come from the DHA-containing microbes, particularly by spray drying the slurry. Typically, at least two thirds of the dry matter in the polar lipid extract of DHA-containing microbes is material derived from the microbial cells; preferably less than 25% of the dry matter is non-microbial, more preferably less than 20%, even more preferably 15% or less. Typically, the spray dried particulate has number average particle size between 5 microns and 10 microns.

In yet another embodiment, this invention provides a method for preparing a DHA-containing particulate material comprising (a) lysing DHA-containing microbial cells; (b) extracting lysed cells with solvent; (c) separating a polar lipid fraction from the extract; and (d) drying the polar lipid fraction, with or without addition of other nutrients, to form a particulate material. Preferably, the polar lipid fraction is an aqueous slurry which is dried by spray drying.

In a particular embodiment, this invention provides a method for preparing a DHA-containing particulate material comprising drying a slurry containing polar lipids extracted from dinoflagellates, wherein the dried material is in the form of particles having a mean particle diameter between 5 and 10 microns.

In yet another embodiment, this invention provides an aqueous emulsion or suspension containing phospholipids with DHA residues obtained from a polar lipid extract from DHA-containing microbes. Preferably, at least 10% of the fatty acid residues in lipids of the DHA-containing microbes are DHA residues. More preferably, at least 10% of the fatty acid residues in polar lipids of the DHA-containing microbes are DHA residues.

In still another embodiment, this invention provides a composition comprising a particulate material containing phospholipids with DHA prepared by drying a slurry comprising (a) a polar lipid extract from DHA containing microbes and (b) a meal containing protein and/or carbohydrate. Preferably, the meal comprises microbial cells or cell fragments, which may be cells or cell fragments which have been extracted to remove part of the lipids, or even most of the lipids. Preferred microbial cells or cell fragments are from *Chlorella, Crypthecodinium,* or a yeast such as *Saccharomyces,* or a fungus, such as *Morteriella, Schizochytrium,* or *Thraustochytrium.*

DETAILED DESCRIPTION OF PREFERRED EMBODIMENTS

Producing high DHA-containing oil from biomass requires several different processing and refining steps. Each refining step produces waste fractions as a byproduct of the oil purification. These byproducts contain significant levels of DHA and other nutrients that can have potential use as aquaculture feeds for fish larvae, bivalves and crustaceans.

One byproduct in particular contains a very high level of DHA as well as other nutrients (carbohydrate, protein, etc) that are useful and valuable in larval nutrition. This byproduct, hereinafter called "DHA Phospholipids," also contains significant levels of all of the amino acids that are considered essential for larvae. The ten amino acids that are generally recognized to be essential for most fish species are histidine, isoleucine, leucine, lysine, methionine, phenylalanine, threonine, tryptophan and valine, see, e.g., Shepherd, Jonathan and Niall Bromage, Intensive Fish Farming, Chapter 5, Nutrition and Growth, Blackwell Scientific Publications, Boston, 1992, pp. 154–197. The DHA Phospholipid material contains all of these amino acids at levels comparable to the levels found in some other aquaculture feeds. The DHA Phospholipid material contains phospholipids having a high proportion of DHA residues, as well as other lipid components such as triglycerides, free fatty acids, sterols, glycolipids, etc. The biochemical composition of the DHA Phospholipids, obtained as spray-dried particles, is given in Table 1. The fatty acid composition of the particulate material is given in Table 2.

Source of DHA-Containing Material

The principal source of DHA in the biosphere is from algae. Numerous algal species produce DHA. One species in particular (*Crypthecodinium cohnii*) has been manipulated to produce very high levels of DHA. This organism has been cultivated at large scale and the biomass has been used for the production of a high DHA-containing oil. Suitable processes for producing DHA-containing biomass from *C. cohnii* are provided in U.S. Pat. Nos. 5,397,591 and 5,492,938, incorporated herein by reference.

Similar DHA Phospholipid material may be made from any single celled organism that contains a significant amount of DHA. This would include various oleaginous fungi, various algae (especially members of the class *Dinophyceae, Bacillariophyceae, Chlorophyceae, Pryinnesiophyceae* and *Euglenophyceae*), as well as organisms of uncertain taxonomic status such as *Thraustochytrium* or *Schizochytrium*. Suitable processes for producing DHA-containing biomass from *Thraustochytrium* or *Schizochytrium* are provided in U.S. Pat. No. 5,130,242, incorporated herein by reference.

Typically, microbes serving as a source of DHA Phospholipids according to this invention will have at least 5% of the fatty acids and fatty acid residues in the microbe as DHA, more typically at least 10%, and preferably at least 20%. Preferably, at least 10% of the fatty acid residues in the polar lipids of the source microbe will be DHA, more preferably at least 20% of the residues will be DHA.

Preparation Methods

DHA Phospholipids may be obtained from a lipid fraction of the DHA-containing biomass. A preferred method for obtaining a suitable lipid fraction is solvent extraction of lysed cells. In a preferred mode, the biomass may be spray-dried, which will lyse most cells, and the spray-dried material extracted with a solvent such as hexane. Grinding or homogenizing the solvent-biomass mixture may facilitate extraction of the lipid fraction (oil) and may also promote recovery of non-lipid components that are desirable for the aquaculture feed. The DHA Phospholipid material is separated from the oil as a water/salt-containing precipitate. Suitable procedures for such separation are readily adapted from analogous processes in vegetable oil refining.

Although the DHA Phospholipid byproduct contains useful levels of DHA and other nutrients, a suitable method must be found to provide this material to larvae. Many fish larvae require live feed, and bivalves and crustaceans also require either live feed organisms or particles of a limited size range. Thus, further processing is preferable to merely providing this material directly to the fish larvae, bivalves or crustaceans.

For those organisms requiring a live feed, the DHA Phospholipids can be fed to artemia and/or rotifers (both natural food organisms for larvae), with the goal of raising the DHA level of the artemia/rotifers and subsequently raising the DHA level of the larvae. For those organisms that are filter feeders, the material may be supplied as small particles and thus provide a direct enrichment of DHA into the diet.

In order to prepare particles of the proper size for ingestion by artemia, rotifers and filter feeders, the DHA Phospholipid material is dried by any suitable process, such as spray drying, granulation, encapsulation and the like. When DHA Phospholipid material was freeze dried, the resultant particles were too large to be useful. The high fat content in the freeze-dried material did not permit the particle size to be reduced by grinding. Spray drying yielded a crumbly mass consisting of particles that were of an appropriate size range for consumption by artemia, rotifers and filter feeders. Mean particle size was determined to be about 5–10 microns in diameter; the distribution of partical sizes about the mean was quite broad (at least from >30 microns to <1 micron). Although the material was subjected to heat during the drying process, the DHA level was not appreciably reduced by the temperature of the dryer. Thus, spray drying yielded a product with a high DHA content and an appropriate particle size.

Preferably, the DHA level of the spray dried material should be maximized, thus making the material an even more valuable source of DHA for larvae. Typically, the DHA level would be raised by increasing the amount of DHA-containing oil in the DHA Phospholipid material, which may be accomplished by adding refined triglyceride oil, partially purified triglycerides or crude lipid extract from a microorganism that is high in DHA. The inventor has noted that, when the triglyceride level (measured as esterified fatty acid level) exceeded about 30% of the total dry weight of the DHA Phospholipid, the material did not spray dry as well and appeared to form very large particles that were less suitable for this application. At triglyceride contents above 40%, the final spray-dried product is very sticky due to the high fat content, which may explain the apparent high particle size. This material is not as easy to handle as the lower triglyceride material, but it still can be used as an artemia and rotifer enrichment product. Of course, supplemental DHA may also be supplied from non-microbial sources, including purified DHA-alkanol esters, but these sources may be less economical.

While DHA Phospholipid may be spray dried directly, spray drying may be facilitated if the slurry contains typical spray drying agents when it is fed into the spray dryer. Suitable spray drying carriers include maltodextrines, starch, gelatin, sugars, and molasses. Preferred carriers include sodium alginate and gum arabic. In addition, various additives whose presence in the final particulate is desirable for nutritional reasons may also be added to the slurry before drying, such as proteins, carbohydrates, fatty acids and lipids, or vitamin sources, including additives like yeast extract, starch, gelatin, gluten, etc. In addition, amino acids may be added to the slurry, such as methionine, a particularly important amino acid in fish nutrition. Alternatively, algal biomass may be added to the slurry as a spray drying aid, preferably using algae which are naturally food for rotifers or fish larvae.

In one embodiment, particulate material may be prepared by formulating and spray drying the DHA Phospholipids with microbial biomass, which may be whole or lysed cells or cellular material after lipid extraction. DHA Phospholipids may be mixed with biomass in any ratio, including 1:100 to 100:1, preferably in ratios from 1:10 to 10:1. The mixture is typically spray dried from an aqueous slurry to form a material with the appearance or consistency of cornmeal. Typically, the biomass will be from microbes that have known nutritional uses, such as *Chlorella*. *Chlorella* is consumed as a human food product, and DHA is an important human nutrient, so such particulate material is also useful in human nutrition. Of course particulate material produced according to this invention may be used to supply DHA in human nutrition whether or not the particulate contains Chlorella, so long as the process conditions and any other additives included in the slurry are suitable for human consumption.

While the DHA Phospholipid is particularly suited to spray drying, particulate material containing high DHA levels may also be prepared according to this invention by granulation or encapsulation. Conditions for granulation or encapsulation of DHA Phospholipid may be readily selected by the skilled worker, typically using one or more of the additives which are listed above for use in spray drying, such as alginate or gum acacia. Of course, DHA Phospolipids may also be coated on oilseed meal (e.g., soybean meal, cotton seed meal, corn germ, etc.). Furthermore, mixtures of DHA Phospholipids with solvent extracted algal biomass ("biomeal") are also suitable for freeze-drying. While this invention is particularly suitable for producing dry products enriched in DHA, the DHA Phospholipids obtained from microbes according to this invention may be formulated in a suspension or emulsion for subsequent use, particularly as a nutritional supplement. Such emulsions or suspensions containing polar lipids may be routinely prepared, as is known in the art.

Particle size distribution in the dried material may be adjusted by fractionation in, e.g., cyclones or filter bags, to remove particles that are too large, but preferably the drying process will produce a particulate material of mean particle size from 5 microns to 10 microns. Typically the dried DHA Phopholipids will be mixed with sea water before feeding to larvae, rotifers, or artemesia. Varying the agitation in this mixing step will permit post-drying adjustment of the particle size.

Another fatty acid with significance in both aquaculture and human and animal nutrition is arachidonic acid (AA). Arachidonic acid may also be obtained in lipid extracts of microbes, although preferred sources of AA are different species from the preferred sources of DHA. Suitable microbial sources of AA and methods for growing them are taught, for example, in U.S. Pat. No. 5,658,767. Extraction of crude lipids from AA-containing microbes leaves a protein-and-carbohydrate containing residue that may also still have appreciable amounts of AA as fatty acids and/or fatty acid residues. This material may be referred to as AA biomeal.

During the processing and refining of the AA-containing crude lipid extract, several fractions are produced, including AA Phospholipids. The AA Phospholipids can also be blended with the DHA Phospholipids to produce a material that contains both fatty acids in the ratio that will provide for optimal nutrition. Such a blend can be prepared as a dry material or as an emulsion or suspension. The AA Phospholipids can also be blended with the DHA biomeal and dried or emulsified to produce a material that is high in arachidonic acid. Through the use of different ratios of DHA Phospholipids, DHA biomeal, AA biomeal, and/or AA Phospholipids, a material can be produced that has the appropriate ratio of DHA and AA for optimal nutrition.

EXAMPLES

In order to facilitate a more complete understanding of the invention, a number of Examples are provided below. However, the scope of the invention is not limited to specific embodiments disclosed in these Examples, which are for purposes of illustration only.

Example 1

Process for Producing DHA Phospholipids

*Crypthecodimium cohnii* is grown by heterotrophic fermentation as described in U.S. Pat. No. 5,407,957, incorporated herein by reference. At the conclusion of the fermentation, the DHA-rich biomass is concentrated by centrifugation to about 18% solids (range is 5–35% solids). The concentrated biomass is held in a chill tank (50–60° F.) prior to spray drying. The material is pumped under high pressure through a spray dryer with an inlet temperature ranging between 300–400° F., but typically 350–380° F. The flow rate into the spray dryer is adjusted as necessary to achieve an outlet temperature of 180–240° F., but typically 205–215° F. The dried biomass recovered from the spray dryer has a moisture content ranging from 1–15% (typically 6%).

The dried biomass is slurried with hexane at the ratio of about 2 liters of hexane per kilogram of dried biomass. The hexane/biomass mixture may be milled in a colloid mill to insure that all cells are broken and that maximum oil can be extracted. Alternatively, the biomass/hexane mixture may be homogenized (e.g., forced through an oriface with pressure drop of approximately 7–800 atm). The hexane fraction (containing the DHA-rich oil) is separated from the solids using a counter current extractor. The hexane exiting from the extractor has an oil content of about 5% (v:v).

The oil/hexane mixture is centrifuged to remove any fine particles that were not previously removed in the extractor. The hexane is partially removed by evaporation to produce a mixture of about 65% oil in hexane. This oil/hexane mixture is cooled to about 40° F. and held at this temperature for about 12 hours. The material that precipitates under the low temperature condition is removed by centrifugation. The remaining hexane associated with the oil is removed by evaporation to produce a hexane-free oil.

The oil is transferred to a refining tank where 50% caustic (0.74% w/w based on oil), 85% phosphoric acid (0.2% w/w based on oil), and oleic acid (to bring the final free fatty acid level to 5% in the oil) are added to the crude oil. The mixture is agitated and heated to approximately 70° F. for 15–30 minutes. The combination of heat and chemicals causes the DHA Phospholipids to precipitate out of the oil. The DHA Phospholipids are collected by centrifugation.

The DHA Phospholipid fraction is homogenized to insure a uniform mixture. At this point the material can be used "as is" for spray drying or it can be blended with various nutrients and other compounds (i.e. vitamins, protein, alginates, antifoams, etc.) before proceeding with spray drying. The solids content of the DHA Phospholipids can range from 10% up to over 80%. Typically, the solids content is diluted to around 25–35% to form a pumpable slurry for spray-drying, although solids content in the slurry may range from 10–50%. The material is spray dried using either a high pressure injection nozzle or a rotary atomizer. Suitable inlet temperatures range between 170–240° F., but typically around 200° F., with the material being fed to the spray dryer at a rate sufficient to maintain an outlet temperature on the spray dryer of 150–200° F., but typically between 180–190° F. In an alternative mode, the slurry is spray dried with inlet temperature of about 300° C. (540° F.) and outlet temperature of about 110° C. (230° F.). Routine optimization of drying conditions by adjustment of inlet temperature and flow rate in view of the guidelines provided herein is contemplated for this invention.

The DHA Phospholipid material collected from the spray dryer has a moisture content of about 4%, and the biochemical composition of three representative batches is given in Table 1, the fatty acid composition of the same 3 batches, plus a 4th is given in Table 2. These batches were all suitable for spray drying. If the esterified fatty acid levels exceed about 30–35%, then the material does not spray dry as well. Rather than forming discrete particles, it tends to form larger clumps, presumably due to the higher oil content in the material.

Example 2

DHA-Containing Particulate Blends

The DHA Phospholipids may be formulated with other materials and nutrients. Table 3 compares spray dried DHA Phospholipids to the composition of DHA Phospholipids+ Biomeal and DHA Phospholipids+Chlorella prepared as follows:

a. DHA-Phospholipids was mixed with biomeal consisting of dried biomass from Example 1 after extraction with solvent, and then spray dried as described in Example 1. The purpose of this blending was to reduce the total fatty acid content of the spray dried material so that it wouldn't be so sticky. This blend was certainly less sticky so it may be considered an improvement to the basic material, even though blending in the biomeal did reduce the total fat content compared to the basic DHA Phospholipids.

b. The DHA Phospholipids were blended with the alga Chlorella, and this mixture was spraydried as described in Example 1. Chlorella is a natural food source for rotifers and is high in protein. By blending with *Chlorella* it was possible to reduce the stickiness of the final spray dried DHA Phospholipids while at the same time providing nutrients from the natural food source. The initial trial was to blend 3:1 (w:w) DHA Phospholipids: Chlorella, and this produced a material that handled very well. A wide ratio of blends is possible. One variation is to have a high ratio of Chlorella to DHA Phospholipids. This would basically provide the natural marine food source with extra DHA, so the material could be as a regular, routine feed and not just as an enrichment to increase the DHA content of the rotifers prior to feeding them to fish larvae.

c. The DHA Phospholipids have also been mixed with a protein source for the purpose of improving the protein content (and therefore nutritional content) of the spray dried material. Specifically, the DHA Phospholipid was blended with soy protein hydrolyzate in a ratio of 3:1 (w:w) of DHA-Phospholipid: soy protein hydrolyzate. This demonstrates that the DHA Phospholipid can be mixed with other nutrients to make a particulate.

Example 3

Blends of DHA and Arachidonic Acid Materials

The DHA Phospholipids can be formulated with arachidonic acid to produce a material that provides both of these fatty acids in a single nutrition product. Arachidonic acid-containing biomass is produced from Morteriella as outlined in U.S. Pat. No. 5,658,767. The Morteriella biomass is harvested by centrifugation and dried under vacuum. The dried biomass is extracted with hexane to remove the arachidonic acid-containing lipids, and the crude lipid fraction is processed in a manner similar to that used in Example 1. The mass remaining after lipid extraction removal (referred to as AA biomeal) contains a high level of protein but also significant amounts of arachidonic acid. This AA biomeal can be blended with the DHA Phospholipids to produce a higher protein material that also contains significant amounts of both arachidonic acid and DHA.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in edible oil extraction and processing, microbial fermentation, nutrition, medicine, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

TABLE 1

Biochemical composition of spray dried DHA Phospholipids

| Component | Prep. 1 | Prep. 2 | Prep 3 |
|---|---|---|---|
| Total Fatty Acid (% of total wt) | 57.4 | 61.3 | 55.6 |
| esterified fatty acid (% of total wt) | 25.6 (48% DHA) | 24.4 (47.7% DHA) | 22.3 (47.9% DHA) |
| free fatty acid (% of total wt) | 31.8 (19% DHA) | 36.9 (22.5% DHA) | 33.3 (25.0% DHA) |
| Sterol (% of total wt) | | | |
| Total Carbohydrate (% of total wt) | 8.0 | 7.2 | 8.3 |
| glucose | 6.1 | 4.7 | 6.2 |
| galactose | 1.9 | 2.5 | 2.1 |
| fucose | 0.0 | 0.0 | 0.0 |

TABLE 1-continued

Biochemical composition of spray dried DHA Phospholipids

| Component | Prep. 1 | Prep. 2 | Prep 3 |
|---|---|---|---|
| Protein (% of total wt) | 13.2 | 9.7 | 11.7 |
| Amino Acid (% of protein) | | | |
| methionine | 2.0 | 4.3 | 2.23 |
| cystine | 0.8 | 1.1 | 0.75 |
| lysine | 4.3 | 3.7 | 4.92 |
| phenylalanine | 5.0 | 5.0 | 1.73 |
| leucine | 8.3 | 8.2 | 7.54 |
| isoleucine | 4.0 | 4.2 | 4.65 |
| threonine | 5.9 | 5.4 | 5.89 |
| valine | 7.2 | 5.4 | 6.99 |
| histidine | 2.5 | 2.2 | 2.56 |
| arginine | 4.8 | 4.3 | 4.74 |
| glycine | 6.2 | 6.2 | 7.05 |
| aspartic acid | 10.4 | 10.3 | 10.66 |
| serine | 5.5 | 6.0 | 6.26 |
| glutamic acid | 13.7 | 13.8 | 14.06 |
| proline | 6.2 | 4.7 | 6.77 |
| hydroxyproline | 0.5 | 1.7 | 0.00 |
| alanine | 7.6 | 8.0 | 8.81 |
| tyrosine | 3.8 | 4.3 | 2.94 |
| tryptophan | 1.4 | 1.2 | 1.46 |
| Moisture (% of total wt) | 4.4 | 4.00 | 6.0 |
| Fiber (% of total wt) | 0.7 | 1.0 | 0.6 |
| Ash (% of total wt) | 10.4 | 10.1 | 10.6 |
| sodium (% of total wt) | 2.6 | not analyzed | 3.38 |
| TOTAL | 94.1 | 93.3 | 92.7 |

TABLE 2

Fatty acid composition of spray dried DHA Phospholipids (% of total fatty acid)

| Fatty Acid | Prep. 1 esterified | Prep. 1 non-esterified | Prep. 2 esterified | Prep. 2 non-esterified | Prep. 3 esterified | Prep. 3 non-esterified | Prep. 4 esterified | Prep. 4 non-esterified |
|---|---|---|---|---|---|---|---|---|
| 08:00 | | | | | 0.06 | | 0.25 | 0.23 |
| 10:00 | 0.67 | 1.22 | 0.83 | 1.11 | 0.45 | 0.76 | 1.39 | 0.5 |
| 11:00 | | | | | | | | |
| 12:00 | 4.34 | 2.69 | 4.36 | 2.65 | 3.34 | 3.14 | 5.71 | 2.71 |
| 13:00 | | | | | | | | |
| 14:00 | 15.94 | 5.81 | 15.52 | 7.7 | 14.83 | 9.68 | 16.71 | 8 |
| 14:01 | 0.13 | | | | 0.12 | | 0.11 | |
| 16:00 | 17.2 | 11.77 | 16.21 | 13.61 | 16.45 | 15.26 | 20.8 | 16.34 |
| 16:01 | 1.7 | 0.47 | 1.63 | 0.6 | 1.4 | 0.53 | 1.16 | 0.46 |
| 16:02 | | | | | | | | |
| 16:03 | | | | | | | | |
| 17:00 | | | | | 0.13 | | | |
| 18:00 | 0.88 | 1.89 | 0.94 | 1.91 | 0.96 | 1.82 | 1.11 | 1.68 |
| 18:1n-9 | 10.21 | 46.29 | 12.82 | 40.61 | 13.29 | 36.1 | 9.22 | 36.97 |
| 18:1n-7 | | 0.62 | | 0.63 | | 0.46 | | 0.56 |
| 18:02 | 0.1 | 8.56 | | 7.47 | 0.4 | 6.06 | 0.1 | 7.3 |
| 18:3n-6 | | | | | 0.27 | | | |
| 18:3n-3 | | 0.12 | | | | | | 0.11 |
| 18:04 | | | | | | | | |
| 20:00 | | 0.09 | | 0.32 | 0.26 | | | 0.09 |
| 20:01 | | 0.15 | | | | | | 0.13 |
| 20:02 | | | | | | | | |
| 20:3n-9 | | | | | | | | |
| 20:3n-6 | | | | | 0.3 | 0.2 | | |
| 20:3n-3 | | | | | | | | 0.61 |
| 20:04 | | | | | | | | |
| 20:05 | | | | | | | | |
| 22:00 | | | | | | | | |
| 22:01 | | | | | | | | |
| 22:04 | | | | | | 0.46 | | 0.42 |
| 22:5n-6 | | | | | 0.64 | | | |
| 22:5n-3 | 0.53 | 0.28 | | | | | | 0.28 |
| 22:06 | 48.05 | 19.62 | 47.68 | 22.52 | 46.96 | 25.01 | 42.85 | 22.78 |
| % Fatty acid in sample | 25.64 | 31.83 | 24.4 | 36.9 | 22.34 | 33.26 | 31.2 | 45.63 |
| % Unknown | 0.23 | 0.41 | 0 | 0.26 | 0.23 | 0.71 | | 1.09 |

TABLE 3A

COMPARISON OF AQUACULTURE PRODUCTS

| Category | DHA Phospholipids | DHA-PL + C.cOHNII | DHA-PL + Chlorella |
|---|---|---|---|
| Total Fatty Acid (%) | 76.8 | 57.3 | 56.7 |
| DHA (% of fat) | 30.9 | 32.91 | 30.54 |
| DHA (% DW) | 23.7 | 18.9 | 17.3 |
| EPA (% of fat) | 0.11 | 0 | 0 |
| Carbohydrate | 2.1 | 18.1 | 9.7 |
| Protein (%) | 11.7 | | 10.2 |
| Moisture (%) | 1.5 | | 2.4 |
| Ash (%) | 9.3 | | 10.8 |
| Fiber (%) | 1 | | 0.8 |
| Total | 102.4 | | 97.2 |

TABLE 3B

FATTY ACID ANALYSIS

| | DHA Phospholipids | DHA-PL + Ccohnii | DHA-PL + Chlorella |
|---|---|---|---|
| Fatty Acid (% of total fatty acid | | | |
| 08:00 | 0.24 | 0.17 | 0.06 |
| 10:00 | 0.86 | 0.64 | 1.06 |
| 11:00 | | | 0.06 |
| 12:00 | 3.93 | 3.41 | 3.23 |
| 13:00 | | 0.00 | |
| 14:00 | 11.54 | 12.05 | 8.61 |
| 14:01 | 0.04 | 0.06 | 0.05 |
| 16:00 | 18.15 | 16.58 | 12.49 |
| 16:01 | 0.74 | 0.96 | 1.18 |
| 16:02 | | | 0.12 |
| 16:03 | | | 0.08 |
| 17:00 | | | |
| 18:00 | 1.45 | 1.42 | 1.87 |
| 18:1n-9 | 25.7 | 26.93 | 33.88 |
| 18:1n-7 | 0.33 | 0.32 | 0.46 |
| 18:02 | 4.38 | 4.58 | 7.46 |
| 18:3n-6 | | | |
| 18:3n-3 | 0.07 | | 0.30 |
| 18:04 | | | |
| 20:00 | 0.05 | | |
| 20:01 | 0.08 | | |
| 20:02 | | | |
| 20:3n-9 | | | |
| 20:3n-6 | | | |
| 20:3n-3 | 0.36 | | |
| 20:04 | | | |
| 20:05 | | | |
| 22:00 | | | |
| 22:01 | | | |
| 22:04 | 0.25 | | |
| 22:5n-6 | | | |
| 22:5n-3 | 0.11 | | |
| 22:06 | 30.93 | 32.91 | 28.85 |
| Total (% fat in fatty acids) | 99.22 | 100.03 | 99.76 |
| % Fatty acid in sample | 76.8 | 57.30 | 56.70 |
| % Unknown | | | |

What is claimed is:

1. A particulate material containing phospholipids with docosahexaenoic acid (DHA) residues and arachidonic acid (ARA) residues prepared by drying a slurry comprising a polar lipid extract from DHA-containing microbes and ARA-containing microbes.

2. The particulate material of claim 1, wherein the mean particle size is between 5 microns and 10 microns.

3. The particulate material of claim 1, wherein the slurry is dried by spray drying.

4. The particulate material of claim 1, wherein at least 10% of the fatty acid residues in lipids of said DHA-containing microbes are DHA residues.

5. The particulate material of claim 1, wherein at least 10% of the fatty acid residues in polar lipids of said DHA-containing microbes are DHA residues.

6. The particulate material of claim 1, wherein said ARA-containing microbes are fungi.

7. The particulate material of claim 1, wherein said ARA-containing microbes are *Morteriella* sp.

8. The particulate material of claim 1, wherein said DHA-containing microbes are dinoflagellates.

9. The particulate material of claim 1, wherein said DHA-containing microbes are *Crypthecodinium cohnii*.

10. A method for preparing a DHA- and ARA-containing particulate material comprising drying a slurry containing polar lipids extracted from dinoflagellates and fungi, wherein the dried material is in the form of particles having a mean particle diameter between 5 and 10 microns.

11. A method for preparing a DHA and ARA-containing particulate material comprising lysing DHA-containing and ARA-containing microbial cells; extracting lysed cells with solvent; separating a polar lipid fraction from the extract; and drying the polar lipid fraction, with or without addition of other nutrients, to form aparticulate material.

12. The method of claim 11, wherein the polar lipid fraction is an aqueous slurry which is dried by spray drying.

13. The method of claim 11, wherein the DHA-containing microbial cells are dinoflagellate cells.

14. The method of claim 11, wherein the DHA-containing microbial cells are *Crypthecodinium cohnii*.

15. The method of claim 11, wherein the ARA-containing microbial cells are fungi cells.

16. The method of claim 11, wherein the ARA-containing microbial cells are cells of *Morteriella* sp.

17. An aqueous emulsion or suspension containing phospholipids with docosahexaenoic acid (DHA) residues and arachidonic acid (ARA) containing residues prepared by Homogenizing with water a polar lipid extract from DHA-containing microbes and ARA-containing microbes.

18. The emulsion or suspension of claim 17, wherein at least 10% of the fatty acid residues in lipids of the DHA-containing microbes are DHA residues.

19. The emulsion or suspension of claim 17, wherein at least 10% of the fatty acid residues in polar lipids of said DHA-containing microbes are DHA residues.

20. The emulsion or suspension of claim 17, wherein said DHA-containing microbes are dinoflagellates.

21. The emulsion or suspension of claim 17, wherein said DHA-containing microbes are *Crypthecodinium cohnii*.

22. The emulsion or suspension of claim 17, wherein said ARA-containing microbes are fungi.

23. The emulsion or suspension of claim 17, wherein said ARA-containing microbes are *Morteriella* sp.

24. A composition comprising a particulate material containing phospholipids with DHA and ARA prepared by drying a slurry comprising a polar lipid extract from DHA-containing microbes and ARA-containing microbes and a meal containing protein, carbohydrate, or both.

25. The composition of claim 24, wherein meal comprises microbial cells or cell fragments.

26. The composition of claim 24, wherein the microbial cells or cell fragments are from Chlorella.

27. The composition of claim 24, wherein the microbial cells or cell fragments are from Crypthecodinium.

28. The composition of claim 24, wherein the microbial cells or cell fragments are from a yeast.

29. The composition of claim 24, wherein the microbial cells or cell fragments are from Morteriella.

30. A method of aquaculture comprising
    feeding particulate material containing a polar lipid extract from microbes comprising phospholipid with DHA residues and phospholipid with ARA residues to live larval feed organisms comprising artemia, rotifers, or a combination thereof to enrich DHA and ARA levels in the larval organisms; and
    feeding DHA- and ARA-enriched live larval organisms to fish larva, bivalves, crustaceans, or a combination thereof.

31. A method of aquaculture comprising
    feeding particulate material containing a polar lipid extract from microbes comprising phospholipid with DHA residues and phospholipid with ARA residues to bivalves and/or crustaceans.

32. The method of claim 30 or 31, wherein particulate material containing phospholipid with DHA residues and ARA residues has mean particulate size from about 5 microns to about 10 microns.

33. The method of claim 30 or 31, wherein particulate material containing phospholipid with DHA residues and ARA residues comprises DHA and EPA in ratio of at least 300:1.

34. The method of claim 30 or 31, wherein particulate material containing phospholipid with DHA residues and ARA residues further comprises vitamins, amino acids, or both.

35. The method of claim 30 or 31, wherein particulate material containing phospholipid with DHA residues and ARA residues further comprises *Chlorella biomass*.

36. The method of claim 30 or 31, wherein particulate material containing phospholipid with DHA residues and ARA residues is prepared by spray-drying a phospholipid-containing byproduct produced in refining a lipid extract from microalgae.

* * * * *

(12) INTER PARTES REEXAMINATION CERTIFICATE (0416th)
United States Patent
Gladue et al.

(10) Number: US 6,812,009 C1
(45) Certificate Issued: Aug. 7, 2012

(54) DHA-CONTAINING NUTRITIONAL COMPOSITIONS AND METHODS FOR THEIR PRODUCTION

(75) Inventors: Raymond M. Gladue, Lexington, KY (US); Paul W. Behrens, Ellicott City, MD (US)

(73) Assignee: Martek Biosciences Corporation, Columbia, MD (US)

Reexamination Request:
No. 95/001,082, Sep. 15, 2008

Reexamination Certificate for:
Patent No.: 6,812,009
Issued: Nov. 2, 2004
Appl. No.: 10/082,340
Filed: Feb. 26, 2002

Related U.S. Application Data

(62) Division of application No. 09/529,021, filed on Apr. 6, 2000, now Pat. No. 6,372,460, which is a continuation of application No. PCT/US98/15835, filed on Jul. 31, 1998.
(60) Provisional application No. 60/054,563, filed on Aug. 1, 1997.

(51) Int. Cl.
| | | |
|---|---|---|
| *A23D 7/005* | (2006.01) | |
| *A23D 9/007* | (2006.01) | |
| *A23D 9/02* | (2006.01) | |
| *A23D 9/05* | (2006.01) | |
| *A23D 9/013* | (2006.01) | |
| *A23K 1/00* | (2006.01) | |
| *A23K 1/16* | (2006.01) | |
| *A23K 1/18* | (2006.01) | |
| *C12P 7/64* | (2006.01) | |
| *C11B 1/10* | (2006.01) | |
| *C11B 1/00* | (2006.01) | |
| *G02B 27/00* | (2006.01) | |

(52) U.S. Cl. ......... 435/134; 426/601; 426/602; 435/254.1; 435/257.3

(58) Field of Classification Search ............ None
See application file for complete search history.

(56) References Cited

To view the complete listing of prior art documents cited during the proceeding for Reexamination Control Number 95/001,082, please refer to the USPTO's public Patent Application Information Retrieval (PAIR) system under the Display References tab.

*Primary Examiner* — Padmashri Ponnaluri

(57) ABSTRACT

This invention provides a particulate material suitable for use as a nutritional supplement, particularly as an aquaculture feed. The particulate material has a high proportion of DHA residues in the lipid fraction, which may be up to 35% of the material, or even more. Preferably, the material has a mean particle size of from about 5 microns to about 10 microns. This invention also provides a method for preparing a particulate material suitable for use as an aquaculture feed from microbial biomass, preferably from algal cells having a high content of DHA residues, by obtaining a lipid fraction from the biomass, preferably by solvent extraction of broken cells, followed by separating a fraction containing phospholipids and proteins from the lipid fraction, and removing water from the protein/phospholipid fraction to form a low moisture particulate, preferably by spray-drying the protein/phospholipid fraction.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-35 are cancelled.
Claim 36 was not reexamined.

\* \* \* \* \*